June 26, 1962 L. F. HAMILTON Re. 25,191

HEMOSTATIC INSTRUMENT

Original Filed Jan. 28, 1957

INVENTOR

LOUIS F. HAMILTON

BY Diggins & LeBlanc

ATTORNEY

United States Patent Office

Re. 25,19

Reissued June 26, 19

25,191

HEMOSTATIC INSTRUMENT

Louis F. Hamilton, 210 S. Roselawn, Artesia, N. Mex.

Original No. 2,970,596, dated Feb. 7, 1961, Ser. No. 636,585, Jan. 28, 1957. Application for reissue Oct. 26, 1961, Ser. No. 148,798

7 Claims. (Cl. 128—326)

Matter enclosed in heavy brackets [ ] appears in the original patent but forms no part of this reissue specification; matter printed in italics indicates the additions made by reissue.

This invention relates to hemostatic instruments and more particularly relates to a simple hemostatic instrument for trying the umbilical cord of new born babies.

The invention has for its object to provide an instrument of the character described which is of extremely simple and efficient construction and whose use reduces the time heretofore required for tying the umbilical cord following child delivery.

It is another object of the invention to provide an instrument of the character described consisting of only two parts having clean and simple lines and being of a rugged construction so that damage thereto is highly unlikely.

Further objects and advantages of the invention will become more apparent upon reference to the following specification and claims and appended drawings wherein:

Figure 1:
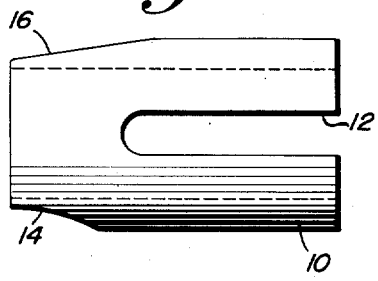
FIGURE 1 is a side elevation of the cylinder of the device of the invention.
Figure 2:
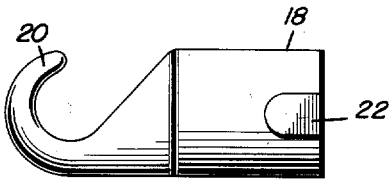
FIGURE 2 is a side elevation of the hooked piston of the device of the invention.
Figure 3:
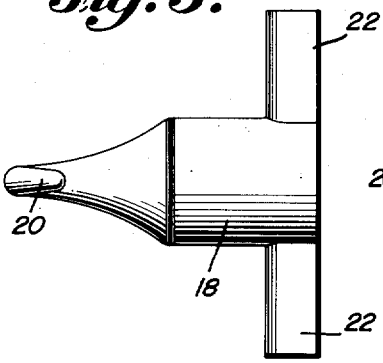
FIGURE 3 is a plan view of the hooked piston of FIGURE 2.

Referring to the figures of the drawing, the hemostatic instrument which comprises my invention consists of a cylinder 10 having slots 12 down the sides thereof and having a rounded and tapered end 14. The upper surface 16 of the rounded and tapered end is flattened for a purpose presently to become apparent.

A hooked piston 18 is provided having a hook 20 at one end thereof and having handles or ears 22 extending radially from one end thereof. The diameter of the hooked piston 18 is such that it fits slidably within the cylinder 10 and the handles 22 are received within the slots 12.

Figure 4:
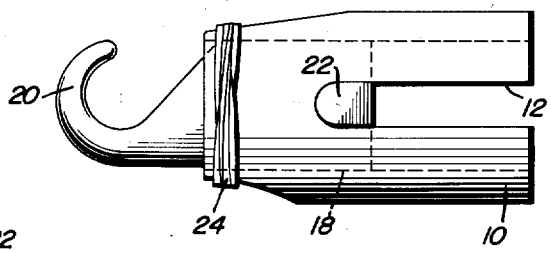
FIGURE 4 is a side elevation of the cylinder and piston in an assembled position ready for use in tying an umbilical cord.
Figure 5:
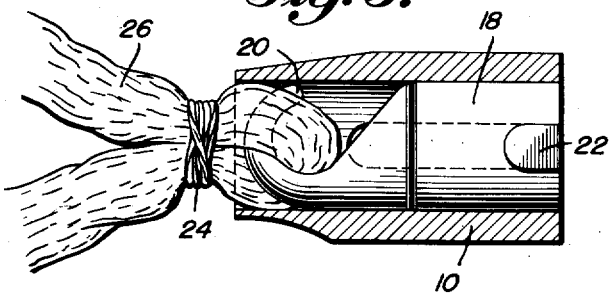
FIGURE 5 is a side elevation, partly in section, showing the device of the invention in use.
Figure 6:
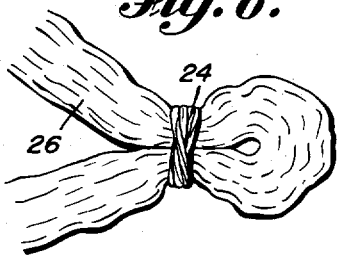
FIGURE 6 is a side elevation showing an umbilical cord tied by means of the device of the invention.

Referring to FIGURE 4, the hooked piston 18 is shown mounted within the cylinder 10 which has a rubber band 24 mounted on the curved tapered end thereof. In use, the umbilical cord to be tied is looped over the hook 20 and the hooked piston is then retracted within the cylinder 10 so as to draw the hook 20 into the rounded end of the cylinder, as is shown in FIGURE 5. At this time the attending physician applies pressure with his thumb on the flat surface 16 on top of the cylinder and simply rolls the rubber band off the tapered end of the cylinder onto the umbilical cord 26. This forms a loop which effectively ties the cord. The hooked piston is then extended by means of the handles 22 until the hook 20 projects from the tapered and curved end of the cylinder, and the umbilical cord is removed from the hook. The umbilical cord has then been effectively tied, as shown in FIGURE 6.

It will be apparent from the foregoing that the hen static instrument of this invention is quite simple in ( eration, is simple in design and susceptible of sturdy c( struction. The device is easily sterilized. It is sm enough so that it may be conveniently carried in physician's bag if so desired.

The invention may be embodied in other specific for without departing from the spirit or essential charact istics thereof. The present embodiment is therefore to considered in all respects as illustrative and not restr tive, the scope of the invention being indicated by 1 appended claims rather than by the foregoing descripti and all changes which come within the meaning and rar of equivalency of the claims are therefore intended to embraced therein.

What is claimed and desired to be secured by Unit States Letters Patent is:

1. A hemostatic instrument for tying umbilical co comprising a cylinder having a tapered end flat on c tapered side, said cylinder being slotted at its other e a piston member slidably mounted in said cylinder a having handle means extending through said slots, a a hook on the end of said piston other than the end which said handle means are attached.

2. A hemostatic instrument according to claim 1 whe in said flat side of said tapered end is positioned adjac the open side of said hook.

3. A hemostatic instrument for tying umbilical co comprising a cylinder having a tapered end flat on c tapered side, said cylinder being slotted at its other e a piston member slidably mounted in said cylinder a having ears extending radially outward therefrom throu said slots, and a hook on said piston at the opposite e thereof from said ears and adapted to extend beyond s tapered end of said cylinder.

*4. A hemostatic instrument for tying umbilical co comprising a housing, a movable hook member exte able from and retractable within said housing, and contractable band received over said housing adjacent s hook member.*

*5. A hemostatic instrument for trying umbilical co comprising a cylinder, a piston member slidable in s cylinder and having a hook on one end thereof, and contractable elastic band on said cylinder.*

*6. A hemostatic instrument for tying umbilical co comprising a cylinder, a piston slidable in said cylin and having a hook extendable from one end of said c inder, means for moving said piston through said c inder, and a contractable elastic band received over s cylinder adjacent said one end.*

*7. A hemostatic instrument for tying umbilical co comprising a cylinder, a piston slidable in said cylin and having a hook extendable from one end of said c inder, handle means on said piston for moving said pist through said cylinder, and a contractable elastic ba received over said cylinder adjacent said hook.*

References Cited in the file of this patent or the original patent

UNITED STATES PATENTS

| | | |
|---|---|---|
| 302,509 | Mauthner | July 22, 18 |
| 823,877 | Kellogg | June 19, 19 |
| 1,625,602 | Gould et al. | Apr. 19, 19 |
| 2,455,833 | Trombetta | Dec. 7, 19 |
| 2,517,361 | Staats | Aug. 1, 19 |
| 2,619,964 | Thaete | Dec. 2, 19 |
| 2,656,580 | Javery | Oct. 27, 19 |
| 2,826,798 | Kahl et al. | Mar. 18, 19 |